United States Patent [19]
Ledford, Jr.

[11] Patent Number: 5,163,215
[45] Date of Patent: Nov. 17, 1992

[54] METHOD OF CONNECTING A TUBE TO A DEVICE FITTING

[75] Inventor: Edward B. Ledford, Jr., Lincoln, Nebr.

[73] Assignee: ICR Research Associates, Inc., Lincoln, Nebr.

[21] Appl. No.: 662,835

[22] Filed: Mar. 1, 1991

[51] Int. Cl.$^5$ ............................................... B23Q 3/00
[52] U.S. Cl. ........................................ 29/468; 29/450; 73/863.85; 285/33; 285/38
[58] Field of Search ................. 29/450, 464, 468; 73/863.85, 23.1; 285/12, 18, 33, 38, 334.2, 334.3, 309, 320; 141/31

[56] References Cited

U.S. PATENT DOCUMENTS

| | | |
|---|---|---|
| 1,175,438 | 3/1916 | Gzupkaytie .................. 285/309 |
| 4,586,732 | 5/1986 | Anderson, Jr. .................. 285/38 X |
| 4,619,473 | 10/1986 | Someya .................. 285/334.3 X |
| 4,637,636 | 1/1987 | Guest .................. 285/38 |
| 4,787,656 | 11/1988 | Ryder .................. 285/334.3 X |

Primary Examiner—Mark Rosenbaum
Assistant Examiner—S. Thomas Hughes
Attorney, Agent, or Firm—Watson, Cole, Grindle & Watson

[57] ABSTRACT

An apparatus for connecting the end of a tubular body, particularly a chromatographic capillary tube, to a detection or injection device fitting comprises a holder having a ferrule for holding said tubular member and an insertion assembly to engage said device fitting. The assembly is adapted to contain the holder and force the ferrule into a seated relation with the device fitting. A method for connecting a tubular member to a device fitting is also provided.

10 Claims, 3 Drawing Sheets

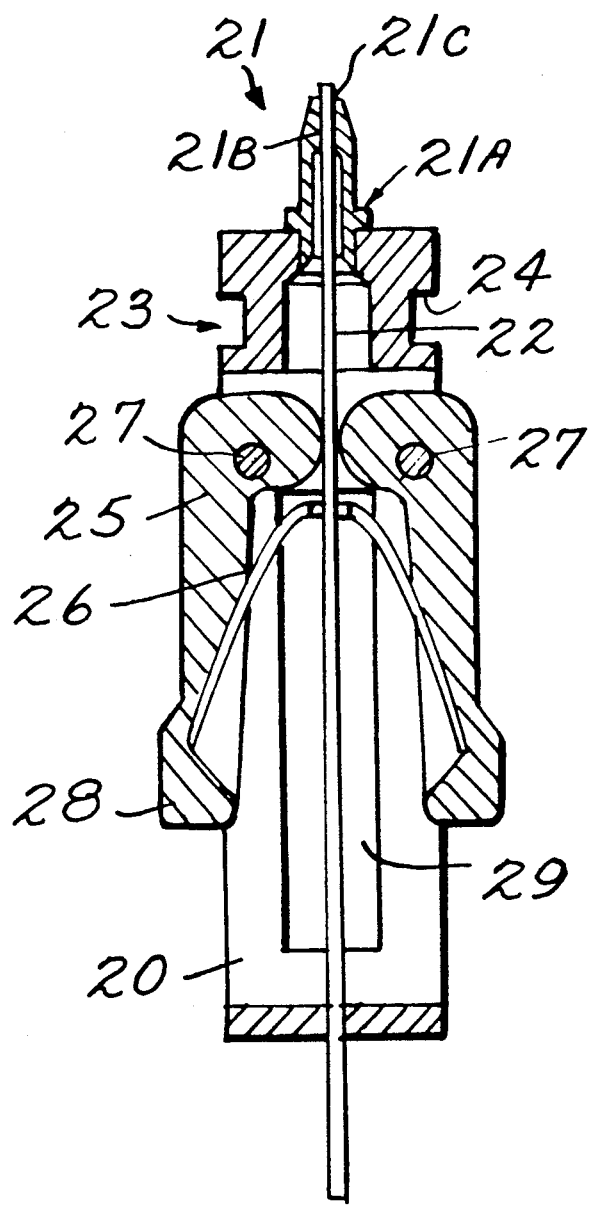
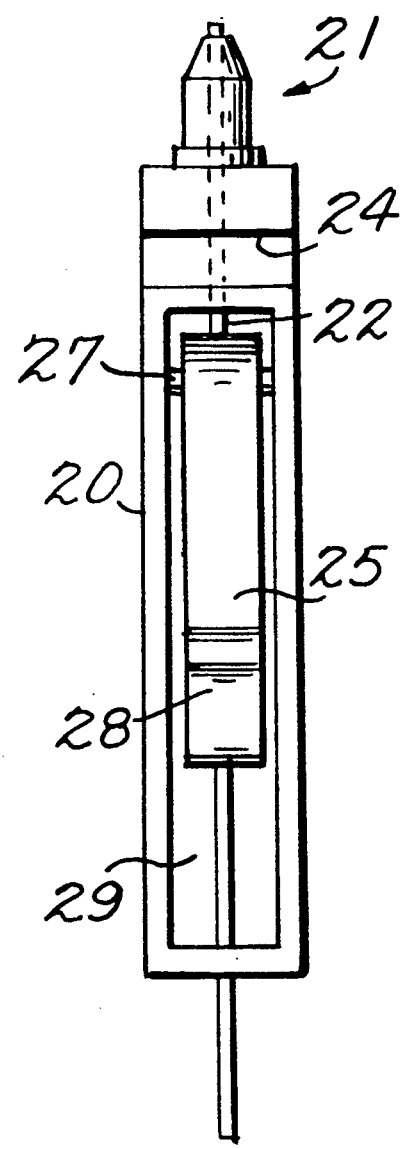

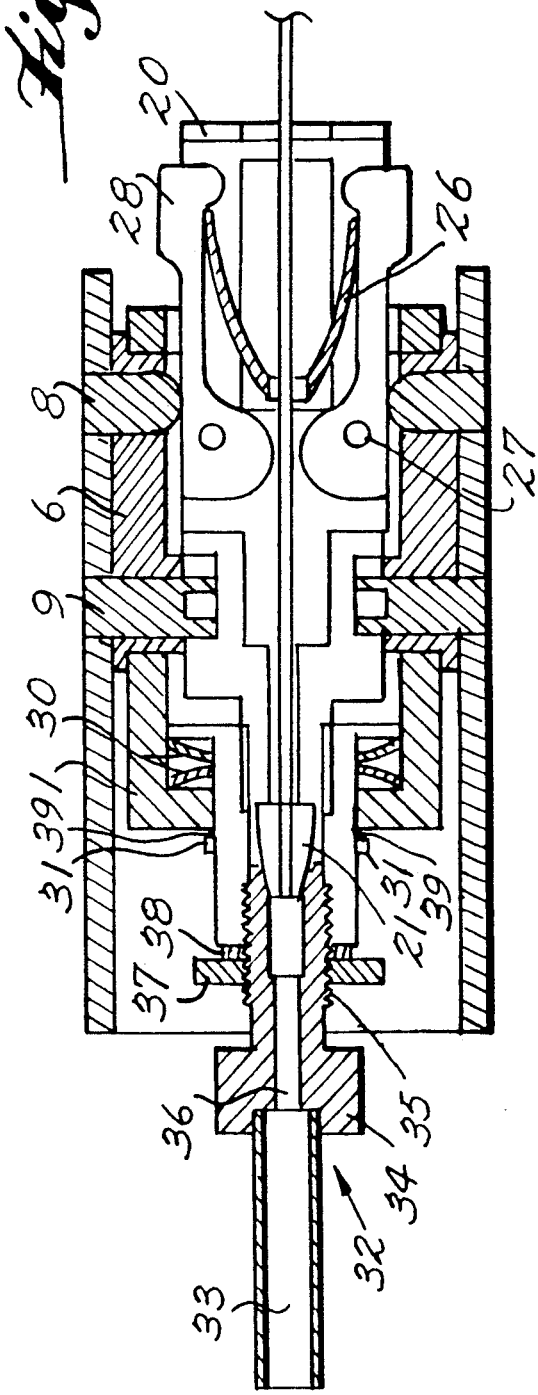
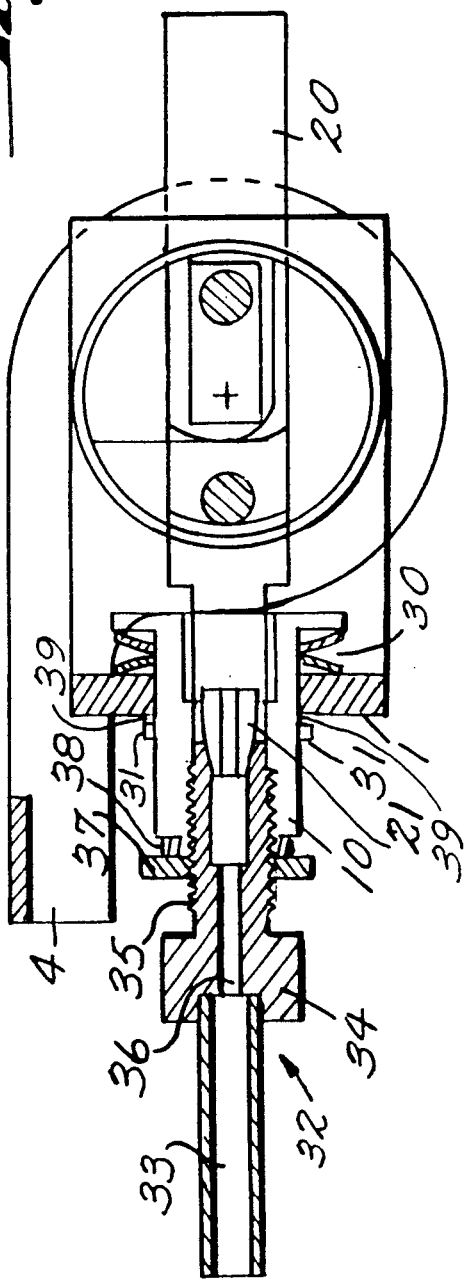

METHOD OF CONNECTING A TUBE TO A DEVICE FITTING

BACKGROUND OF THE INVENTION

The present invention relates to a connection for a tubular member and more particularly to an end connection for a capillary tube. The invention moreover relates to a quick-connect for a chromatographic capillary tube column.

In one class of chromatographic methods, electrically neutral analytes are entrained by a mobile fluid which carries them down the bore of a capillary tube or column. Analytes undergo partitioning between this mobile fluid, or mobile phase, and a stationary phase coating the inner wall of and/or packing interior to, the capillary bore. In this class of chromatography, the mobile phase may be gas, liquid or supercritical fluid giving rise to methods and apparatus commonly known as capillary gas chromatography, microbore liquid chromatography or supercritical fluid chromatography, respectively.

In another class of chromatographic methods, electrically charged analytes are propelled by an electric field through a stationary phase filling the bore of a capillary tube. This class of methods and apparatus is commonly known as capillary zone electrophoresis.

In prior art forms of capillary chromatography, capillary columns are sealed into sample injector means and sample detection means using tapered deformable seals or ferrules through which the columns are inserted The ferrules are deformed under pressure supplied by an external torqued hexagonal nut, which forces the ferrule taper against a tapered metallic seat such that the ferrule contracts radially about the capillary column inserted through the ferrule, thus effecting a tight seal. Ferrules of this type are preferably high-temperature plastic deformable ferrules Graphite-Vespel ® ferrules are preferred.

In chromatography, it is important to be able to quickly connect the ends of a chromatographic column to both an injection device for feeding a sample and a detection device for analyzing the sample after it has travelled through the length of the column. It is also important to be able to quickly change capillary tubes.

One process of changing a capillary gas chromatographic column has been widely employed. A nut and ferrule are slipped over the end of a capillary tube. Following insertion through the ferrule, the operator cleaves a small length of capillary tube from the end of the column to be sure the operative column end is open and free of small particles or ferrule shavings which would obstruct the flow of mobile phase during chromatographic separation. The operator then gathers the nut and ferrule together along the length of the column, and draws the end of the column into proximity to the forward end of the ferrule. Immobilizing the column position relative to the ferrule end with one hand, the operator paints a mark on the column near the back of the nut using, for example, Liquid Paper ®, commonly used to cover typographical errors in typed documents. The operator then memorizes the position of the spot relative to the back of the nut. The nut/ferrule/column combination is then inserted into, for example, an injector port of a capillary gas chromatograph. The nut is tightened partially, and the column pulled to align the painted spot to its original position relative to the rear of the hexagonal nut. This positions the end of the capillary tube relative to the ferrule tip, a positioning critical to proper function of the injection means. The nut is then tightened. This procedure is repeated for the other end of the column, which is sealed into a detector port.

Methods of this type for sealing capillary columns into gas chromatographs suffer numerous disadvantages. Considerable manual dexterity is required of the operator to position the end of the column in proper spatial relation to the ferrule tip. Because columns are mounted in oven structures that are generally small and positioned below shoulder height on laboratory benches, operators must perform dexterous operations in cramped regions while bending over, in the case of top loading ovens, or squatting down and straining upwards in the case of front loading ovens. It is not uncommon for the nut and ferrule assembly to slip at some point in the installation process, often becoming entangled or mechanically engaged with wire frame cages on which columns are mounted, with resulting inconvenience and occasional column damage. Threaded fittings and nuts wear out and have to be replaced, further adding to the cost and inconvenience of known gas chromatographs. Column positioning errors commonly cause dead volume in injectors or detectors, which leads to undesirable tailing of chromatographic peaks. In capillary column manufacturing operations, particularly quality testing, in which large numbers of columns must be connected and disconnected on a daily basis, operator fatigue can reduce overall production efficiency and increase production costs. Wrenches used to tighten ferrule nuts are often dropped, resulting in damage to expensive capillary columns. Also, operators often accidentally paint fingers and gloves with the marking fluid.

The aforementioned disadvantages, which present problems in capillary gas chromatography, also present problems in other forms of capillary chromatography.

SUMMARY OF THE INVENTION

It is an object of this invention to provide a means of connecting capillary columns to chromatographs and a method which overcome the above-mentioned disadvantages.

It is a further object of this invention to provide a capillary quick-connect system which requires no tools for installation and operation.

It is a still further object of this invention to provide a capillary quick-connect that supplies torque-free, longitudinal sealing force upon a sealing ferrule.

It is yet a further object of this invention to provide a capillary quick-connect system that is lightweight, and which presents negligible thermal load to the capillary column.

It is yet a further object of this invention to provide a capillary quick-connect system that captures a ferrule in a holder assembly.

It is yet a further object of this invention to provide a ferrule which guides a column through its central bore.

It is yet a further object of this invention to provide a column holder assembly.

It is yet a further object of this invention to provide a column holder assembly that can immobilize a column relative to a ferrule captured by the holder assembly.

It is yet a further object of this invention to provide a column holder assembly which permits an operator to easily cut a fresh column end, easily position the column end relative to the tip of a captured ferrule, and easily immobilize the column within the holder assembly in proper spatial relation to the column tip.

It is yet a further object of this invention to provide a lever operated insertion assembly capable of accepting a column holder assembly and transmitting torque-free insertion and sealing force thereto.

It is still a further object of this invention to provide a capillary quick-connect which, when in its operational configuration, makes no mechanical contact with the capillary column except at the ferrule seal.

It is yet a further object of the invention to provide a capillary quick-connect assembly that exposes the column to oven atmosphere, which assembly itself can be exposed to oven atmosphere, and which is inexpensive and easy to operate.

In accordance with the above and further objects of the invention, a capillary quick-connect system comprises a column holder and an insertion assembly.

The present invention has several advantages. The column holder eliminates free slippage of parts along the column, and breaks the installation process into a series of small steps that can be performed rapidly, without demand upon the operator. The quick-connect will greatly reduce operator bending and straining. The position of the column relative to the ferrule tip can be set accurately, and will not slip, eliminating time consuming correction of column positioning error. The quick-connect eliminates threaded parts which wear out, thus reducing consumables cost. External tools, e.g., wrenches, and associated hazards to expensive capillary columns are eliminated. The invention preserves, and indeed simplifies, the necessary practice of cutting fresh column ends to avoid clogging. No torque is transmitted to the column. Columns stored with column holders can be rapidly exchanged.

BRIEF DESCRIPTION OF THE DRAWINGS

The above noted and other features of the invention will be better understood when considered with reference to the accompanying drawings, in which:

FIG. 2 is a cross-sectional view of the column holder assembly according to the present invention;

FIG. 3 is a side view of the column holder assembly according to the present invention;

FIG. 4 is cross-sectional view of the holder assembly inserted and locked into the insertion assembly according to the present invention;

FIG. 5 is a side cross-sectional, and partially transparent view of the assembly shown in FIG. 4.

DETAILED DESCRIPTION OF PREFERRED EMBODIMENTS

Figure 1:
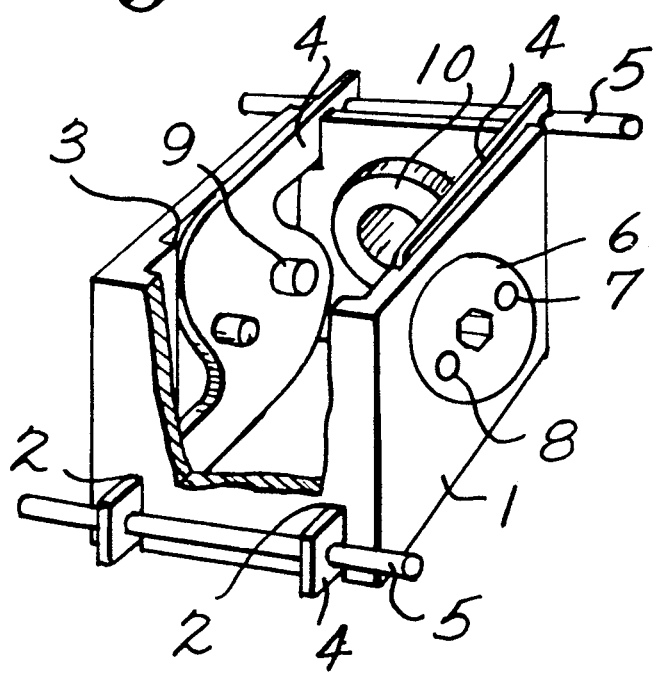
FIG. 1 is a partially broken away perspective drawing of the insertion assembly according to the present invention.

The present invention provides a connection for a tubular member, particularly a capillary tube. According to the invention, the connection is easy to use and quickly connects the end of a tube to a standard fitting in a locking relation.

In one embodiment of the present invention, a tube holder, or column holder for chromatographic applications, holds a tube by gripping action. When the tube is to be connected to a device fitting, the holder is inserted into an insertion assembly which can be activated to a closed and locked position. In this position, the assembly provides a sealed and firm connection of the tube to the device fitting.

According to the present invention, a column holder is provided which captures a ferrule at its forward end. Preferably, a pair of spring-biased pivoted grips of jaws interior to the column holder clamp the column and immobilize it when the jaws are released. Depressing the jaws frees the column so that it can slide relative to the ferrule. The column holder assembly carries engaging means, preferably a pair of notches, or shoulders, to which longitudinal insertion and sealing force can be applied.

In operation, the jaws of the column holder are opened by depressing them between the thumb and forefinger of one hand. The column is inserted through the ferrule. The jaws are released, immobilizing the column, the end of which is cut off using methods commonly practiced in the art. The operator again depresses the jaws, positions the column relative to the ferrule, and releases the jaws. Finally the operator inserts the column holder into the insertion assembly, flips the lever integral thereto, and installs the column. To remove the column, the operator releases the lever. There is no need to separate the column from the holder assembly. The operator caps the column and stores it for future use, leaving the holder in place to facilitate later reinstallation.

The insertion assembly preferably comprises a fitting having an opening through which a material or a tube or liner can travel. In chromatography, injection and detection devices usually have threaded fittings to which the insertion assembly engages. The assembly, therefore, preferably also comprises a threaded fitting, most preferably a threaded spindle. Other fittings known to those of skill in the art may be employed.

When a threaded spindle is used, a test piece of column approximately three inches long is inserted into the holder and the holder, carrying the piece of column, is inserted into the insertion assembly. The lever is then rotated to the closed and locked position and the insertion assembly together with the locked holder containing the length of column is screwed onto the device fitting until the length of column is sealed. It is this action that sets the sealing force. A locknut is then preferably employed to lock the spindle and device fitting together in the relation such that a tight fit between the ferrule of the holder and the spindle/fitting combination is held.

Once the insertion assembly fitting and the device fitting have been engaged, the lever is opened and the holder containing the length of column is removed. The length of column is then removed from the holder. The column to be sealed may then be inserted into the holder and immobilized therein by gripping action. The holder with the column to be sealed is then inserted into the insertion assembly and the lever is activated to secure the holder within the insertion assembly. This also deforms the ferrule in the end of the holder into sealed relation with the column and the device fitting. Material travelling out of the end of the tube can then pass through the assembly fitting and device fitting without leakage. If material is to be passed into the tube from an injection device, the same type of fitting relation is used to provide a tight connection which does not leak. Preferably, the tube holder is provided with a ferrule end fitting. A tube is passed through the gripping means then through the ferrule and held in place by action of the gripping means until locked in the insertion assembly.

Once the holder is inserted into the insertion assembly, a lever on the insertion assembly is rotated, causing engaging means connected to the lever to move into contact with engaging means of the holder assembly. For example, a cam may displace the holder longitudinally toward the injector or detector port loading a belleville spring, which transmits sealing force to the end of the holder, preferably a ferrule. Secondary means, also caused to be moved as the lever is activated, depress the jaws of the column holder shortly after the ferrule sealing force is applied, thus freeing the column from mechanical contact with any portion of the assembly but the ferrule.

In a preferred embodiment, the lever device comprises at least one lever handle and means connected to the handle to move the holder device and force the ferrule thereof into a tightly sealed relation with the column and the device fitting. The lever may be connected to a rotating member to which is connected at least one means for engaging the holder assembly and moving it into a sealed relation with the device fitting. The rotating member may be geared and actuated by a pinion or worm drive. If the engaging means are connected to the rotating member off center of the member's axis of rotation, once engaged, the holder is forced to move toward the assembly fitting through cam action.

The engaging means of the insertion assembly preferably comprises a protrusion on the rotating member. Preferably, the means comprise a roller which can rotate about an axis off center to the axis of rotation of the rotating member.

The engaging means of the insertion assembly mates with corresponding engaging means on the holder. If a protrusion is used for the engaging means of the rotating member, a corresponding recess may be formed on the holding device in which the protrusion mates and can transfer an applied force. An opposite relation may also be used or other well known engaging means.

FIG. 1 shows a partially cut away perspective view of an insertion assembly according to the present invention comprising a frame 1 in which notches 2 and recesses 3 are machined to accommodate a pair of "S" shaped lever arms 4. The lever arms 4 are connected by handles 5. A pair of rotors 6 are imbedded in holes machined into the side of the frame 1.

In the center of each rotor is a hexagonal opening whose center defines the axis of rotation of the rotor. The lever arms may be opened by rotating the rotors with an allen wrench. Thus, handling of potentially hot lever arms is avoided. Each lever arm has a roller axle 7, and a rounded pin 8 diametrically opposed thereto. The roller axle 7 captures a roller 9 near the inner surface of each lever arm 4.

The insertion assembly attaches to an injector or detector port of a chromatograph via a spindle 10, which is machined to adapt to the particular fittings used in the chromatograph.

In chromatographs, injection and detection devices are provided with injector and detector ports, respectively. At these ports are fittings such as a Swagelok ® fittings to which a device according to the present invention may connect. Swagelok fittings are depicted as 32 in FIGS. 4 and 5. These fittings consist of a nipple 33, a hex nut portion 34 and an exterior threaded portion 35. A passageway 36 is provided which extends through the center of the fitting 32 through which a sample flows to a detection device or from an injection device.

The fitting 32 threadably engages the interior threads of the spindle 10 as shown in FIGS. 4 and 5. A lockwasher 38 and locknut 37 share the exterior threads 35 of the fitting 32 with the spindle 10 and prevent the fitting and spindle from unscrewing and disengaging while maintaining the proper force on the ferrule 21.

In FIG. 1, the lever arms 4 are shown in the closed and locked position. Prior to locking, the lever is rotated 90 degrees from the position shown in FIG. 1 and the column holder is inserted into the insertion assembly through a hole in the bottom thereof. The lever is then returned to the position shown in FIG. 1.

FIGS. 2 and 3 show side-sectional views of the column holder assembly comprising a holder body 20 into which a ferrule 21 is threaded. The ferrule exterior is stepped at step 21a, and its interior is bored and tapered so as to guide a capillary column 22 through its center bore 21b. The top of the holder is counter-bored so as to continue the interior guiding taper of the ferrule 21 into the counter-bore of the holder. The top of the holder is notched on either side at notch 23, providing shoulders 24 which are engaged by the roller 9 of the insertion assembly when the lever 4 of the insertion assembly is brought to the closed position. A pair of jaws 25 are biased normally closed by a V-shaped spring 26, and rotate freely on a pair of pivots 27. Finger pads 28 near the bottoms of the jaws, when depressed, cause the upper portions thereof to separate, thus releasing the column 22. When the fingerpads 28 are released, the jaws 25 close under spring pressure and grip the column 22. The jaws are polished smooth so as not to gouge or score the exterior of the capillary column 22. The jaws may be made of metal, ceramic, or of high temperature plastic, as for example, polyimide. A cutout 29 extending over most of the holder body 20 exposes the column 22 to the heated atmosphere of a gas chromatographic oven, thereby reducing thermal load upon the column.

FIGS. 4 and 5 show the closed quick-connect assembly with the holder inserted and locked into position. The holder shown here has been simplified for clarity. The roller 9 rotates into the notch 23 near the top of the column holder, transmitting upward force against the shoulder 24. An equal and opposite force is exerted downward upon the roller 9. This downward force component is transmitted via the rotor 6 to the frame 1, which, because it slips over the spindle 10, is forced downward as well, toward the flange at the bottom of the spindle 10. Because the spindle 10 is locked to the chromatographic fitting 32 by a locknut 37, and is stationary, downward movement of the frame compresses a pair of belleville springs 30 disposed between the underside of the topmost portion of the frame and the spindle flange. The belleville springs 30 supply sealing force to the ferrule 21. Preload on the belleville springs is maintained with a snap ring 31, which engages a groove in the exterior of the spindle 10, and locks the frame into preload position. A gap 39 exists between the snap ring 31 and the frame 1 when the assembly is in the locked position.

To install the quick-connect assembly, a short piece of column is immobilized in the holder. The holder is inserted into the insertion assembly and the lever rotated to the closed position. A locknut is threaded onto the injector or detector port fitting. The entire assembly is threaded onto the chromatograph inlet or detector port fitting by hand, until the ferrule seals, as indicated by firm tug on the short length of column which will not move if sealed. The locknut is then turned by hand down onto the spindle. The levers are then opened, the short length of the column removed, and the column to be used is inserted into the holder. After cutting a fresh end, the column end is positioned relative to the ferrule tip 26, locked by releasing the jaws 28, and inserted into the insertion assembly. Closing the levers 4 of the insertion assembly completes column installation.

In practice it is found that this assembly produces reliable and repeatable sealing force with little or no need for readjustment following installation. Positioning a column in the holder and making it ready for insertion takes about five seconds. Inserting the holder and locking it takes about three seconds.

From the above description, it can be understood that the technique has several advantages over prior capillary connection schemes.

While the present invention is particularly useful for coupling capillary tubing and for chromatographic applications, it is to be understood that the devices according to the present invention can be useful for coupling tubing of any diameter and type if appropriate dimensions of the insertion assembly, column (tube) holder, and corresponding fittings are provided.

While preferred embodiments have been described with some particularity, many modifications and variations to those embodiments are possible without deviating from the invention defined in the appended claims.

What is claimed is:

1. A method of installing a quick-connect assembly onto a device port wherein a sealing relationship between a tube and said device port can be set and held, said method comprising the steps of:

positioning a tube in a ferrule, said ferrule being captured by a holder, thereby forming a holder assembly;

positioning said holder assembly in an insertion assembly;

moving an engagement means thereby locking said holder assembly within said insertion assembly;

installing onto said device port said insertion assembly with said holder assembly locked thereinto by engaging a spindle integral with said insertion assembly with said device port such that, as said tube and said device port are brought into a sealing relationship,
   (a) a spring integral with said insertion assembly is compressed,
   (b) a compressive force arising from compression of the spring is transmitted to said ferrule, and
   (c) compression of said ferrule causes said sealing relationship; and bringing into locking relationship said device port and said spindle thereby making said sealing relationship maintainable and repeatable.

2. A method as in claim 1 wherein a lock-nut is threadably engaged upon said device port and said step of bringing into locking relationship comprises screwing said lock-nut into engagement with said spindle.

3. A method of sealing a tube having an end and a diameter to a device port equipped with an insertion assembly, said insertion assembly having a body, a spindle, a spring, and an engagement means for engaging a holder assembly, said holder assembly comprising said tube, a holder, and a ferrule having an end and a central bore, said method comprising:

positioning said ferrule in said holder;

inserting said end of said tube through the central bore of said ferrule;

positioning said tube end with respect to said ferrule end, thereby forming said holder assembly;

positioning said holder assembly in said insertion assembly;

moving said engagement means thereby engaging said insertion assembly with said holder assembly wherein
   (a) a spring integral with said insertion assembly is compressed, thereby causing said spindle to move with respect to said body,
   (b) a compressive force arising from compression of said spring is transmitted to said ferrule, and
   (c) compression of said ferrule brings said tube and said device port into sealing relationship.

4. The method as in claim 3, wherein said moving step comprises moving a lever connected to said engagement means.

5. A method as in claim 4, wherein said engagement means comprises cams.

6. A method as in claim 5, wherein said moving step comprises rotating said cams about an axis substantially congruent with said diameter of said tube.

7. A method as in claim 6, wherein said cams supply substantially longitudinal, torque-free sealing force to said holder assembly.

8. A method as in claim 3, further comprising the steps of:

following said insertion step and prior to said moving step cutting off said end of said tube thereby forming a fresh tube;

positioning said fresh tube end with respect to said ferrule end such that slippage of said tube with respect to said ferrule end is substantially prevented thereby forming said holder assembly.

9. A method as in claim 8, further comprising the steps of:

depressing spring biased tube gripping means integral to said holder assembly thereby permitting free slippage of said tube in said holder assembly;

releasing said spring biased tube gripping means thereby immobilizing said tube within said holder assembly.

10. A method as in claims 3, wherein said insertion step is aided by a guiding taper interior to said holder assembly.

* * * * *